US009007050B2

(12) United States Patent
Hill (10) Patent No.: US 9,007,050 B2
(45) Date of Patent: Apr. 14, 2015

(54) SOIL MOISTURE SENSOR WITH IMPROVED ENCLOSURE (75) Inventor: Jason Lester Hill, Capistrano Beach, CA (US)

(73) Assignee: The Toro Company, Bloomington, MN (US)

( * ) Notice: Subject to any disclaimer, the term of this patent is extended or adjusted under 35 U.S.C. 154(b) by 288 days.

(21) Appl. No.: 13/235,207

(22) Filed: Sep. 16, 2011

(65) Prior Publication Data

US 2012/0068688 A1 Mar. 22, 2012

Related U.S. Application Data (60) Provisional application No. 61/384,190, filed on Sep. 17, 2010.

(51) Int. Cl.
G01N 27/00 (2006.01)
G01N 33/24 (2006.01)
G01N 27/04 (2006.01)

(52) U.S. Cl.
CPC ............ *G01N 33/246* (2013.01); *G01N 27/048* (2013.01)

(58) Field of Classification Search
CPC ... A01G 25/167; A01G 25/16; A01G 27/001; A01G 29/00; G01N 33/246; G01N 27/223; G01N 33/24; G01N 22/04; G01N 15/0826; G01N 2021/855; G01N 27/046
See application file for complete search history.

(56) References Cited

U.S. PATENT DOCUMENTS

| 2,688,056 | A | 8/1954 | Kettering et al. |
|---|---|---|---|
| 2,866,379 | A | 12/1958 | Veit |
| 3,372,899 | A | 3/1968 | McPherson |
| 3,639,770 | A | 2/1972 | Zizelmann |
| 3,751,173 | A | 8/1973 | Sanz et al. |
| 3,783,804 | A | 1/1974 | Platz |
| 3,787,703 | A | 1/1974 | Topol |
| 3,794,992 | A | 2/1974 | Gehman |
| 3,808,385 | A | 4/1974 | Klinefelter |
| 3,900,396 | A | 8/1975 | Lamadrid |
| 4,064,507 | A | 12/1977 | Schmitz |
| 4,122,389 | A * | 10/1978 | Haagen ..................... 324/694 |
| 4,176,395 | A | 11/1979 | Evelyn-Veere et al. |
| 4,184,789 | A | 1/1980 | Gilde, Jr. |

(Continued)

FOREIGN PATENT DOCUMENTS

| EP | 0126031 A2 | 11/1984 |
|---|---|---|
| GB | 2247951 A | 3/1992 |

(Continued)

OTHER PUBLICATIONS

WIPO, U.S. International Search Authority, International Search Report and Written Opinion mailed Jan. 9, 2013 in International Patent Application No. PCT/US2012/061718, 9 pages.

(Continued)

*Primary Examiner* — Vinh Nguyen
(74) *Attorney, Agent, or Firm* — Inskeep IP Group, Inc.

(57) ABSTRACT

A wireless soil sensor includes a curved surface and at least two groups of sensor-pin electrodes. A tine-catching block is disposed within the sensor body, near a top of the sensor to protect against aeration tools damaging components of the sensor. The electrical circuitry and the battery are separately potted in an epoxy material and oriented vertically, creating a central gap through which an incoming aeration tine is directed.

13 Claims, 9 Drawing Sheets

(56) References Cited

U.S. PATENT DOCUMENTS

| | | |
|---|---|---|
| 4,209,131 A | 6/1980 | Barash et al. |
| 4,264,902 A | 4/1981 | Miller |
| 4,274,705 A | 6/1981 | Miller |
| 4,306,805 A | 12/1981 | Arrington |
| 4,313,042 A | 1/1982 | Ehrhart |
| 4,396,149 A | 8/1983 | Hirsch |
| 4,405,085 A | 9/1983 | Meyer |
| 4,422,714 A | 12/1983 | Benoit et al. |
| 4,430,646 A | 2/1984 | Enemark |
| 4,445,788 A | 5/1984 | Twersky et al. |
| 4,567,563 A | 1/1986 | Hirsch |
| 4,655,076 A | 4/1987 | Weihe et al. |
| 4,674,681 A | 6/1987 | Meis et al. |
| 4,684,920 A | 8/1987 | Reiter |
| 4,693,419 A | 9/1987 | Weintraub et al. |
| 4,726,239 A | 2/1988 | Boggess et al. |
| 4,760,547 A | 7/1988 | Duxbury |
| 4,803,470 A | 2/1989 | Fineman |
| 4,814,608 A | 3/1989 | Dempsey et al. |
| 4,823,168 A | 4/1989 | Kamahori et al. |
| 4,847,781 A | 7/1989 | Brown, III et al. |
| 4,852,802 A | 8/1989 | Iggulden |
| 4,852,804 A | 8/1989 | Baier et al. |
| 4,862,701 A | 9/1989 | Small et al. |
| 4,867,379 A | 9/1989 | Hunter |
| 4,898,332 A | 2/1990 | Hunter et al. |
| 4,916,642 A | 4/1990 | Kaiser et al. |
| 4,922,433 A | 5/1990 | Mark |
| 4,937,732 A | 6/1990 | Brundesini |
| 4,940,974 A | 7/1990 | Sojka |
| 4,956,835 A | 9/1990 | Grover |
| 4,967,961 A | 11/1990 | Hunter |
| 4,974,552 A | 12/1990 | Sickafus |
| 5,005,005 A | 4/1991 | Brossia |
| 5,058,806 A | 10/1991 | Rupar |
| RE33,823 E | 2/1992 | Nelson et al. |
| 5,087,886 A | 2/1992 | Mann |
| 5,101,083 A | 3/1992 | Tyler et al. |
| 5,104,045 A | 4/1992 | Kah, Jr. |
| 5,148,990 A | 9/1992 | Kah, Jr. |
| 5,150,622 A | 9/1992 | Vollweiler |
| 5,209,129 A | 5/1993 | Jaselskis et al. |
| 5,251,153 A | 10/1993 | Nielsen et al. |
| 5,299,742 A | 4/1994 | Han |
| 5,333,785 A | 8/1994 | Dodds |
| 5,355,122 A | 10/1994 | Erickson |
| 5,385,297 A | 1/1995 | Rein et al. |
| 5,408,893 A | 4/1995 | Mcleroy |
| 5,418,466 A | 5/1995 | Watson |
| 5,424,649 A * | 6/1995 | Gluck et al. ................ 324/667 |
| 5,442,435 A | 8/1995 | Cooper et al. |
| 5,445,178 A | 8/1995 | Feuer |
| 5,465,904 A | 11/1995 | Vaello |
| 5,471,671 A | 11/1995 | Wang et al. |
| 5,499,024 A | 3/1996 | Germanton et al. |
| 5,526,982 A | 6/1996 | McKenzie |
| 5,598,977 A | 2/1997 | Lemme |
| 5,635,710 A | 6/1997 | Reed et al. |
| 5,667,336 A | 9/1997 | Zur |
| 5,726,644 A | 3/1998 | Jednacz et al. |
| 5,737,318 A | 4/1998 | Melnik |
| 5,740,031 A | 4/1998 | Gagnon |
| 5,740,038 A | 4/1998 | Hergert |
| 5,749,521 A | 5/1998 | Lattery |
| 5,778,332 A | 7/1998 | Chang et al. |
| 5,813,606 A | 9/1998 | Ziff |
| 5,821,864 A | 10/1998 | Knop et al. |
| 5,836,339 A | 11/1998 | Klever |
| 5,853,122 A | 12/1998 | Caprio |
| D407,656 S | 4/1999 | Klever |
| 5,898,733 A | 4/1999 | Satyanarayana |
| 5,909,429 A | 6/1999 | Satyanarayana et al. |
| 5,926,101 A | 7/1999 | Dasgupta |
| 5,978,364 A | 11/1999 | Melnik |
| 6,005,517 A | 12/1999 | Friedrichs |
| 6,016,971 A | 1/2000 | Welch |
| 6,028,857 A | 2/2000 | Poor |
| 6,061,440 A | 5/2000 | Delaney et al. |
| 6,073,427 A | 6/2000 | Nichols |
| 6,079,433 A | 6/2000 | Saarem |
| 6,088,621 A | 7/2000 | Woytowitz et al. |
| 6,097,703 A | 8/2000 | Larsen et al. |
| 6,126,093 A | 10/2000 | Grether et al. |
| 6,145,755 A | 11/2000 | Feltz |
| 6,195,108 B1 | 2/2001 | Kanno |
| 6,208,247 B1 | 3/2001 | Agre et al. |
| 6,212,388 B1 | 4/2001 | Seo |
| 6,254,828 B1 | 7/2001 | Lacount |
| 6,275,500 B1 | 8/2001 | Callaway, Jr. et al. |
| 6,283,139 B1 | 9/2001 | Symonds et al. |
| 6,298,285 B1 | 10/2001 | Addink et al. |
| 6,312,191 B1 | 11/2001 | Rosenfeld |
| 6,314,340 B1 | 11/2001 | Mecham et al. |
| 6,401,530 B1 | 6/2002 | Roman |
| 6,401,742 B1 * | 6/2002 | Cramer et al. ................ 137/78.3 |
| 6,452,499 B1 | 9/2002 | Runge |
| 6,453,215 B1 | 9/2002 | Lavoie |
| 6,504,834 B1 | 1/2003 | Fifield |
| 6,553,336 B1 | 4/2003 | Johnson et al. |
| 6,570,109 B2 | 5/2003 | Klinefelter et al. |
| 6,600,971 B1 | 7/2003 | Smith et al. |
| 6,601,440 B1 | 8/2003 | Chuang |
| 6,634,225 B1 | 10/2003 | Reime |
| 6,652,188 B1 | 11/2003 | Albright |
| 6,660,971 B2 | 12/2003 | Terada et al. |
| 6,665,278 B2 | 12/2003 | Grayson |
| 6,685,104 B1 | 2/2004 | Float |
| 6,690,452 B2 | 2/2004 | Wilks, Jr. |
| 6,705,553 B2 | 3/2004 | Drechsel |
| 6,752,362 B1 | 6/2004 | Gretz |
| 6,768,422 B2 | 7/2004 | Schofield et al. |
| 6,782,310 B2 | 8/2004 | Bailey et al. |
| 6,784,988 B2 | 8/2004 | Vijayakumar et al. |
| 6,842,430 B1 | 1/2005 | Melnik |
| 6,855,947 B2 | 2/2005 | Graves et al. |
| 6,892,114 B1 | 5/2005 | Addink et al. |
| 6,895,987 B2 | 5/2005 | Addink et al. |
| 6,907,787 B2 | 6/2005 | Cook et al. |
| 6,947,132 B1 | 9/2005 | Boss et al. |
| 6,977,351 B1 | 12/2005 | Woytowitz |
| 6,997,642 B2 | 2/2006 | Bishop, Jr. |
| 7,012,394 B2 | 3/2006 | Moore et al. |
| 7,032,836 B2 | 4/2006 | Sesser et al. |
| 7,037,554 B2 | 5/2006 | Tao et al. |
| 7,058,040 B2 | 6/2006 | Schmidt |
| 7,086,608 B2 | 8/2006 | Perkins |
| 7,100,842 B2 | 9/2006 | Meyer et al. |
| 7,114,376 B2 | 10/2006 | Loucks |
| 7,143,957 B2 | 12/2006 | Nelson |
| 7,159,795 B2 | 1/2007 | Sesser et al. |
| 7,172,366 B1 | 2/2007 | Bishop, Jr. |
| 7,189,960 B2 | 3/2007 | Zimmerman |
| 7,191,955 B2 | 3/2007 | Ivans |
| 7,240,743 B2 | 7/2007 | Buss et al. |
| 7,247,837 B2 | 7/2007 | Zimmerman |
| 7,261,245 B2 | 8/2007 | Zur |
| 7,264,177 B2 | 9/2007 | Buck et al. |
| 7,281,439 B2 | 10/2007 | Schmitt et al. |
| 7,286,935 B2 | 10/2007 | Aspola et al. |
| 7,339,957 B2 | 3/2008 | Hitt |
| 7,413,380 B2 | 8/2008 | Corwon et al. |
| 7,719,432 B1 * | 5/2010 | Hill ................................ 340/602 |
| 7,788,970 B2 * | 9/2010 | Hitt et al. ........................ 73/73 |
| 7,789,321 B2 | 9/2010 | Hitt |
| 2001/0033559 A1 | 10/2001 | Masui |
| 2001/0049563 A1 | 12/2001 | Addink et al. |
| 2002/0002425 A1 | 1/2002 | Dossey |
| 2002/0029111 A1 | 3/2002 | Peek |
| 2002/0100814 A1 | 8/2002 | Pollak |
| 2002/0112531 A1 | 8/2002 | Hubbell |
| 2002/0123351 A1 | 9/2002 | Miyoshi |
| 2002/0139868 A1 | 10/2002 | Sesser et al. |
| 2002/0144453 A1 | 10/2002 | Su |
| 2003/0037167 A1 | 2/2003 | Garcia-Luna-Aceves et al. |

(56) References Cited

U.S. PATENT DOCUMENTS

| | | |
|---|---|---|
| 2003/0067889 A1 | 4/2003 | Petite |
| 2003/0092442 A1 | 5/2003 | Dalal |
| 2003/0114204 A1 | 6/2003 | Allen et al. |
| 2004/0030456 A1 | 2/2004 | Barlow |
| 2004/0039489 A1 | 2/2004 | Moore |
| 2004/0071125 A1 | 4/2004 | Gross |
| 2004/0083833 A1 | 5/2004 | Hitt et al. |
| 2004/0100394 A1 | 5/2004 | Hitt |
| 2005/0079831 A1 | 4/2005 | Ramachandran |
| 2006/0054214 A1 | 3/2006 | Caamano |
| 2006/0127183 A1 | 6/2006 | Bishop, Jr. |
| 2006/0178847 A1 | 8/2006 | Glancy |
| 2007/0237583 A1 | 10/2007 | Corwon |
| 2008/0129495 A1 | 6/2008 | Hitt |
| 2008/0255708 A1 | 10/2008 | Nies et al. |
| 2010/0268392 A1 | 10/2010 | Korol et al. |

FOREIGN PATENT DOCUMENTS

| | | |
|---|---|---|
| JP | S63294145 A | 11/1988 |
| JP | 2002168674 A | 10/2010 |
| WO | WO2006/001734 A1 | 1/2006 |

OTHER PUBLICATIONS

United States Patent and Trademark Office, Office Action mailed Jun. 30, 2011 in U.S. Appl. No. 11/207,220, 17 pages.
United States Patent and Trademark Office, Final Office Action mailed May 5, 2011 in U.S. Appl. No. 12/186,454, 12 pages.
United States Patent and Trademark Office, Office Action mailed Apr. 13, 2011 in U.S. Appl. No. 12/634,554, 9 pages.
United States Patent and Trademark Office, Notice of Allowance mailed Mar. 2, 2011 in U.S. Appl. No. 12/855,615, 10 pages.
United States Patent and Trademark Office, Office Action mailed Nov. 17, 2010 in U.S. Appl. No. 12/855,615, 13 pages.
United States Patent and Trademark Office, Notice of Allowance mailed Jun. 30, 2010 in U.S. Appl. No. 11/220,289, 4 pages.
United States Patent and Trademark Office, Notice of Allowance mailed May 28, 2010 in U.S. Appl. No. 10/693,017, 14 pages.
United States Patent and Trademark Office, Final Office Action mailed Apr. 28, 2010 in U.S. Appl. No. 12/186,454, 9 pages.
United States Patent and Trademark Office, Final Office Action mailed Feb. 23, 2010 in U.S. Appl. No. 10/693,017, 9 pages.
United States Patent and Trademark Office, Notice of Allowance mailed Feb. 11, 2010 in U.S. Appl. No. 12/104,937, 11 pages.
United States Patent and Trademark Office, Office Action mailed Jan. 12, 2010 in U.S. Appl. No. 11/220,289, 7 pages.
United States Patent and Trademark Office, Office Action mailed Jun. 30, 2009 in U.S. Appl. No. 11/220,289, 7 pages.
United States Patent and Trademark Office, Office Action mailed May 12, 2009 in U.S. Appl. No. 10/693,017, 8 pages.
United States Patent and Trademark Office, Final Office Action mailed Dec. 9, 2008 in U.S. Appl. No. 11/220,289, 9 pages.
United States Patent and Trademark Office, Final Office Action mailed Nov. 25, 2008 in U.S. Appl. No. 10/693,017, 10 pages.
United States Patent and Trademark Office, Office Action mailed May 7, 2008 in U.S. Appl. No. 10/693,017, 10 pages.
United States Patent and Trademark Office, Office Action mailed Jan. 24, 2008 in U.S. Appl. No. 11/220,289, 6 pages.
United States Patent and Trademark Office, Final Office Action mailed Oct. 24, 2007 in U.S. Appl. No. 10/693,017, 6 pages.
United States Patent and Trademark Office, Notice of Allowance mailed Oct. 16, 2007 in U.S. Appl. No. 10/692,518, 8 pages.
United States Patent and Trademark Office, Office Action mailed May 9, 2007 in U.S. Appl. No. 10/692,518, 8 pages.
Culler, David et al., "Overview of Sensor Networks", IEEE Computer, Special Issue in Sensor Networks, Aug. 2004, pp. 41-49.
United States Patent and Trademark Office, Office Action mailed Apr. 13, 2004 in U.S. Appl. No. 10/693,017, 9 pages.
Chakeres, Ian D. et al., "AODV Routing Protocol Implementation Design", Proceedings of the International Workshop on Wireless Ad Hoc Networking (WWAN), Tokyo, Japan, Mar. 2004.
Hill, Jason Lester, "System Architecture for Wireless Sensor Networks", PhD Thesis published at the University of California at Berkeley, 2003, pp. 1-186.
Dukes et al., Residential Irrigation System Rainfall Shutoff Devices, University of Florida IFAS Extension, 7 pages, Aug. 2002.
IEEE, "Wireless Medium Access Control (MAC) and Physical Layer (PHY) Specifications for Wireless Personal Area Networks (WPANS)," IEEE Std 802.15.1(TM) -2002, 2002, 9 pages, IEEE.
Gutierrez et al., "IEEE 802.15.4: Developing Standard for Low-Power Low-Cost Wireless Personal Area Networks", IEEE Network, Sep. 1, 2001, 8 pages, IEEE.
E-mail of Feb. 27, 2001 from Alicia Rodriguez, Product Manager for Rain Bird's Clemar manufacturing Corp., 2nd largest manufacturer of irrigation products, and rain sensors in the world.
E-mail of Feb. 14, 2001 from Steve Tyler, Buckner, Inc., who is also Patentee of U.S. 5,101,083.
E-mail of Feb. 13, 2001 from Darren Redatzke, Sr., Marketing Manager for Toro, Inc., world's largest manufacturer of irrigation products and rain sensors.
E-mail of Feb. 6, 2001 from "Wally", Managing Director of Holman Industries, the largest manufacturer or irrigation controllers in Australia.
Advertising copy from archive.org for "R&D Engineering Wireless Rain Sensor Products" by R&D Engineering, copyright 2000, rainsensor.com, 2 pages.
Trenholm et al., How to Calibrate Your Sprinkler System1, University of Florida IFAS Extension, 4 pages, Jan. 2001.
Hill, Jason et al., "System Architecture Directions for Networked Sensors", ASPLOS-IX, Cambridge, Massachusetts, Nov. 2000.
"Presenting the Wireless RainSensor for Irrigation systems" brochure by R&D Engineering, copyright 2000, rainsensor.com, 5 pages.
"The Wireless RainSensor for Irrigation Systems" brochure by R&D Engineering, copyright 2000, rainsensor.com, 8 pages.
Maltz, David A., et al., "Experiences Designing and Building a Multi-Hop Wireless Ad Hoc Network Testbed," Mar. 5, 1999, 22 pages, School of Computer Science, Carnegie Mellon University, Pittsburgh, Pennsylvania.
Garcia-Luna-Aceves, J.J. et al., "Wireless Internet Gateways (WINGS)," 1997, 7 pages, University of California at Santa Cruz, Department of Computer Engineering, Santa Cruz, California.
"Application of Fuzzy Logic in an Irrigation Control System" -Zhang et al, Auburn University, IEEE 1996.
Rain Bird, Maxicom Guide to Operations, Chapter 7, Oct. 1994, US.
Rain Bird, Maxicom Central Control System, Irrigation Management Designed to Fit Your Needs Jun. 1994, pp. 2-8, Rain Bird Sales, Inc., US.
Rain Bird, Components of the Maxicom System, Feb. 9, 1994, p. 3.2, Section 3,US.
Rain Bird, Any Time Any Where Any Controller, Central Output Module, 1994, Rain Bird Sales, Inc., 4 pages.
Rain Bird, Maxicom Central Computer Control System, "Landscape Irrigation Products, 1993-1994 Catalog," pp. 98-99, US.
Brownrigg, E., "User Provided Access to the Internet," Nov. 30-Dec. 2, 1992, Proceedings of The Fifth International Conference on New Information Technology, Hong Kong.
Rain Bird, Maxicom Central Control System Guide to Operations, Table of Contents and pp. 5.4-1-2; 5.4-41-42; 7.2-1-2, Rain Bird Sales, Inc., US.
Daly, J., Ed., "Distribution, Networks, and Networking: Options for Dissemination," Jun. 9-10, 1992, 7 pages, Workshop on Electronic Texts-Session III Proceedings, Library of Congress, Washington, D.C.
"An Automated Data Acquisition System for Modeling the Characteristics of a Soil Moisture Sensor" -Posada et al, IEEE, vol. 40, No. 5. Oct. 1991.
Shacham, N., et al., "A Packet Radio Network for Library Automation," Oct. 19-22, 1987, pp. 456-462, Proceedings of the 1987 IEEE Military Communications Conference. (MILCOM '87), New York: IEEE Press vol. 2.

(56) References Cited

OTHER PUBLICATIONS

Lynch, Clifford A. et al., Packet Radio Networks, 1987, 276 pages, University of California, Berkeley, California.

Jubin, John, et al., "The DARPA Packet Radio Network Protocols," Jan. 1987, pp. 21-34, Proceedings of the IEEE, vol. 75, No. 1.

Westcott, J.A., "Issues in Distributed Routing for Mobile Packet Radio Networks," 1982, pp. 233-238, IEEE.

Kahn, R.E., "The Organization of Computer Resources into a Packet Radio Network," Jan. 1977, pp. 169-178, IEEE Transactions on Communications, vol. 25, No. 1.

* cited by examiner

SOIL MOISTURE SENSOR WITH IMPROVED ENCLOSURE

RELATED APPLICATIONS

This application claims priority to U.S. Provisional Application Ser. No. 61/384,190 filed Sep. 17, 2010 entitled Wireless Soil Moisture Sensor, the contents of which are incorporated in their entirety herein.

BACKGROUND OF THE INVENTION

Soil moisture sensors typically include one or more electrodes that are placed in contact with soil at a specific location. A sensor measures electrical values on the electrodes, determines a moisture value, and then communicates these values back to an irrigation controller.

However, these moisture sensors can be difficult to properly install in the soil. Improper installation can lead to inaccurate or misleading moisture data. Further, these moisture sensors are susceptible to damage from grounds keeping equipment. Such damage can result in water leakage into the soil moisture sensor, damaging the sensitive internal electronics.

SUMMARY OF THE INVENTION

In a preferred embodiment, the present invention comprises a wireless soil sensor having a curved surface and at least two groups of sensor-pin electrodes. A tine-catching block 120 is disposed within the sensor body, near a top of the sensor to protect against aeration tools damaging components of the sensor. The electrical circuitry and the battery are separately potted in an epoxy material and oriented vertically, creating a central gap through which an incoming aeration tine is directed.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1-14 illustrates various views of a wireless soil moisture sensor 100 according to the present invention. As discussed in greater detail below, aspects of the sensor 100 allow for improved installation into a soil location resulting in more representative soil measurements. Additionally, other aspects allow for greater damage resistance, especially from turf maintenance equipment (e.g., soil aerators, mowers, etc.).

Figure 1:
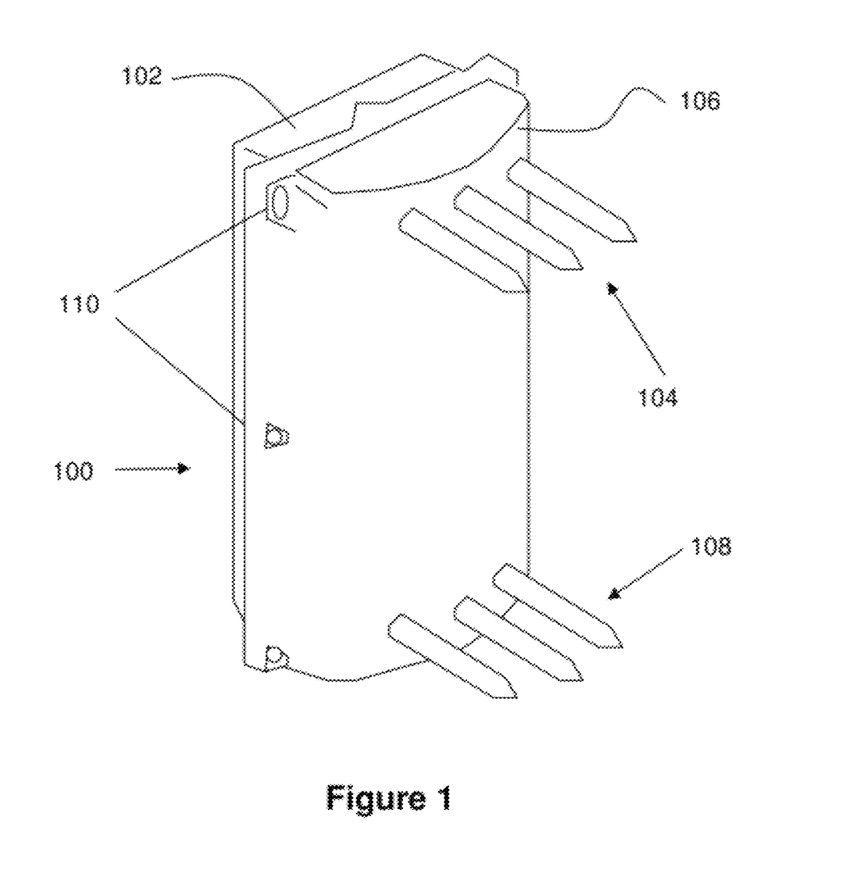
FIG. 1 illustrates a front perspective view of a wireless moisture sensor according to the present invention.
Figure 2:
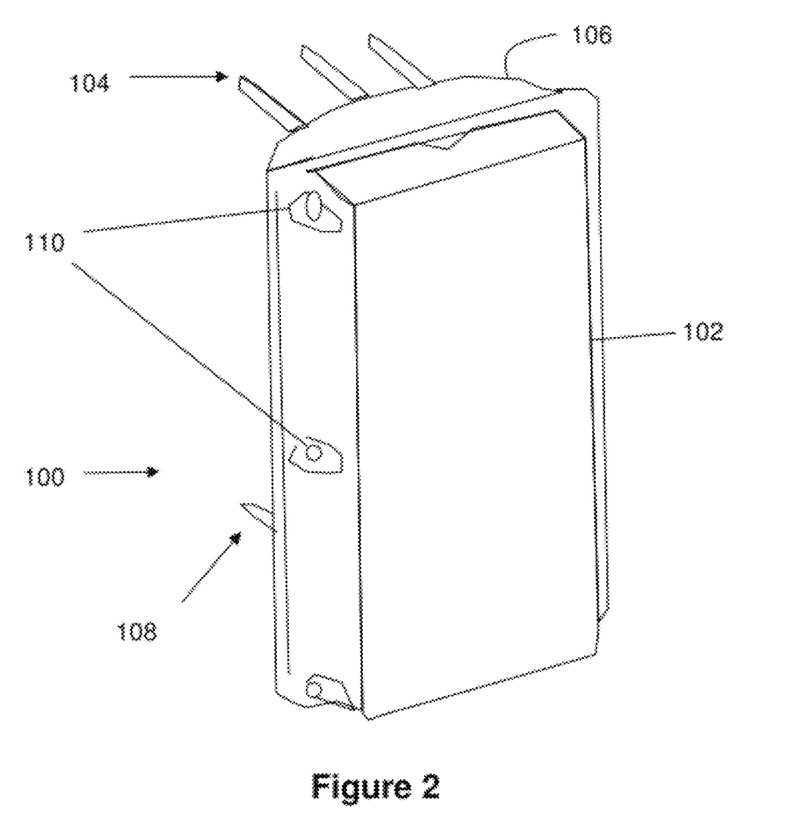
FIG. 2 illustrates a back perspective view of the wireless moisture sensor of FIG. 1.
Figure 3:
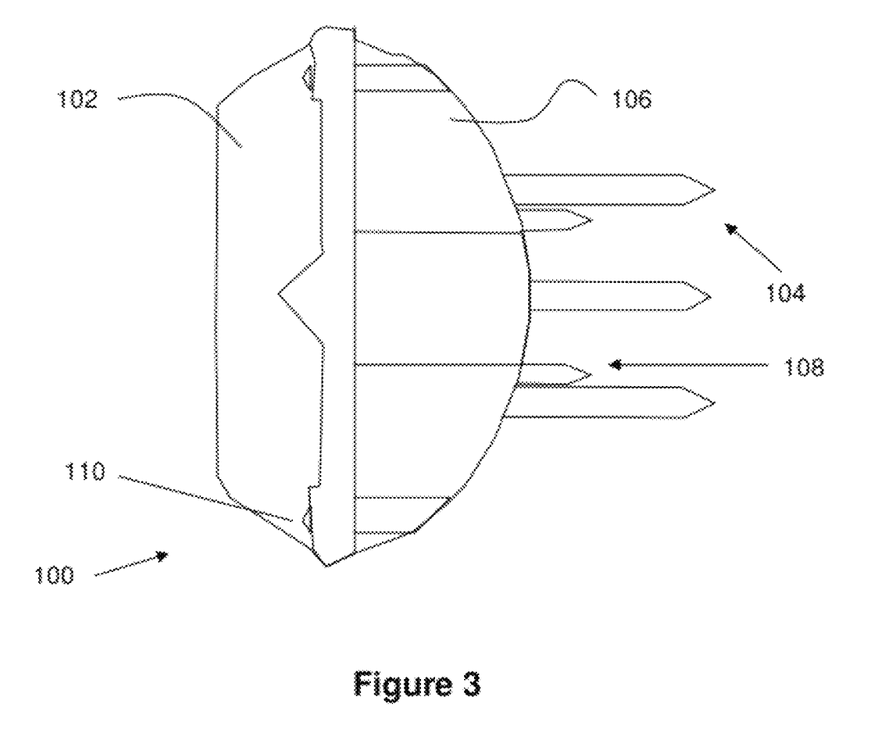
FIG. 3 illustrates a top view of the wireless moisture sensor of FIG. 1.

As best seen in FIGS. 1-3, the sensor 100 comprises an outer casing or body that is formed by a generally flat, back case member 102 and a relatively curved or partially cylindrical front case member 106. Both case members 102 and 106 are preferably coupled together with screws 110, a silicon seal and a tongue-in-groove coupling along an outer perimeter of the case members 102 and 106.

The front case member 106 also includes a top row of elongated electrodes 104 and a bottom row of elongated electrodes 108. Preferably, each row includes three electrodes, which allow internal sensor circuitry to measure soil moisture and soil salinity. As seen in FIG. 3, the ends of these electrodes 104, 108 are preferably even with each other (i.e., they have varying lengths to compensate for the curved surface of the front case member 106). However, the electrodes may also have the same length such that the middle electrodes extend further than those on the ends (i.e., following the curve).

Figure 4:
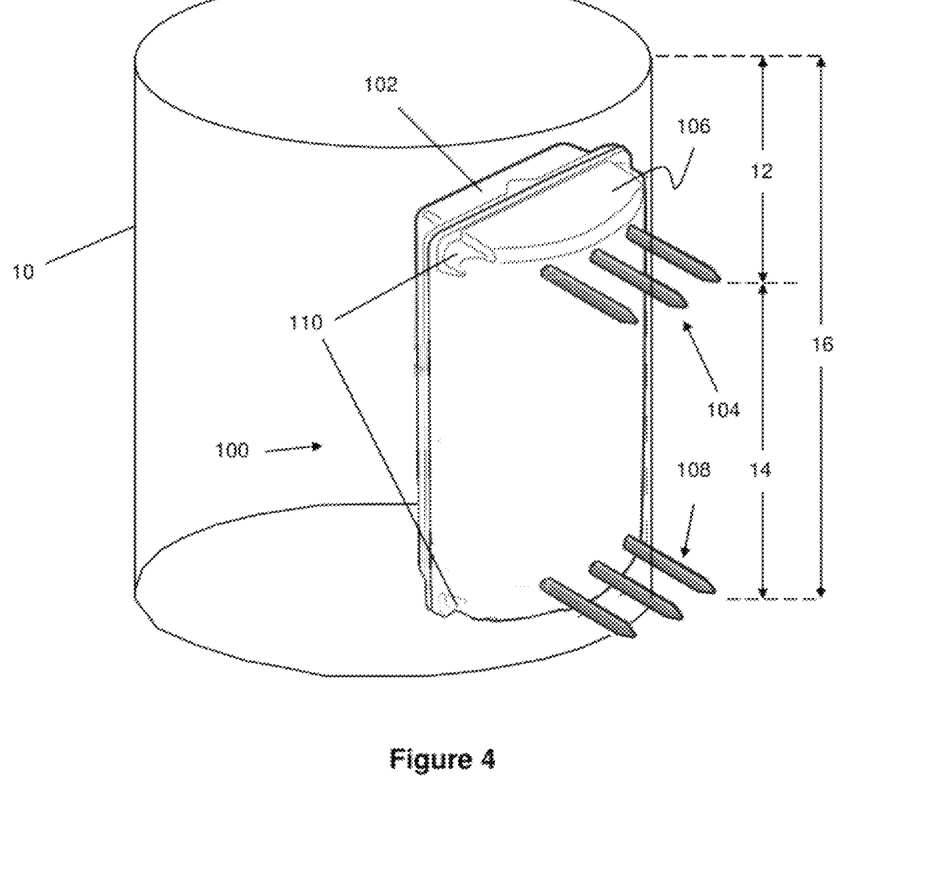
FIG. 4 illustrates a perspective view of the wireless moisture sensor of FIG. 1 in a 4.25" cylindrical hole.

Preferably, the front case member 106 is curved such that it matches the curve of a hole created by a golf course "cup cutting" tool. For example, the curve may match that of a 4.25" hole, commonly used on golf courses. As best seen in FIG. 4, the sensor 100 is placed within the 4.25" hole 10 such that the curved surface of the case member 106 is pressed against the curved sidewall of the hole 10. In this respect, the electrodes 104 and 108 infiltrate undisturbed areas of soil adjacent to the hole. Since the soil adjacent to the hole is undisturbed, it will likely provide a more representative measurement of the nearby soil compared with a measurement from disturbed soil filled in immediately around the body of the sensor 100.

Preferably, the top sensor pins 104 are positioned between about 2-4 inches from the top of the ground (length 12). The bottom sensor pins 108 are preferably located about 5" below the top pins 104 (length 14) and therefore may be located between about 7-9" from the top of the ground (length 16). This positioning typically locates the top sensor pins 104 in the center of the root zone for the grass or similar turf while the lower sensor pins 108 may be located below near the lower end of the root zone to help track salt build-up and infiltration rates. Often, compressed and uncompressed soil will retain different amounts of water.

Figure 5:
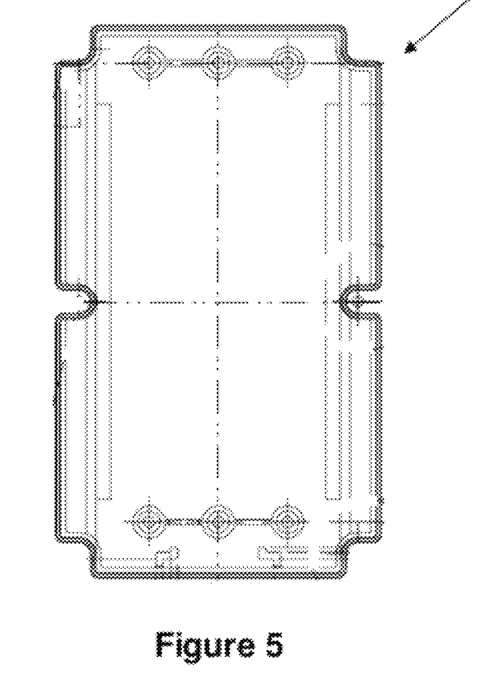
FIGS. 5-7 illustrate various views of a front case member of the wireless moisture sensor of FIG. 1.
Figure 6:
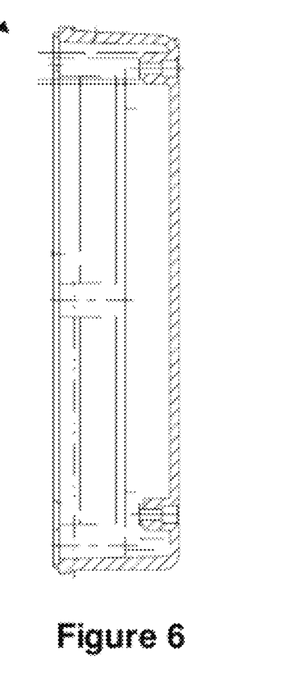
Figure 7:
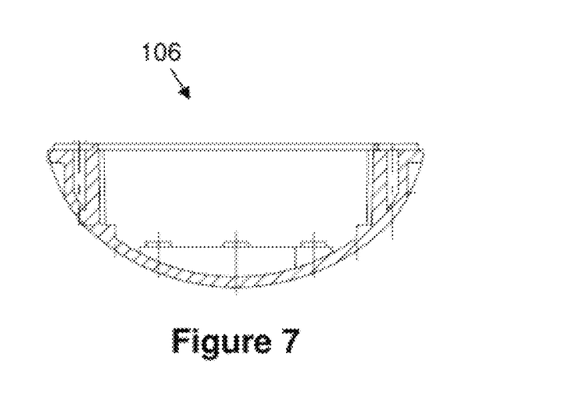
Figure 8:
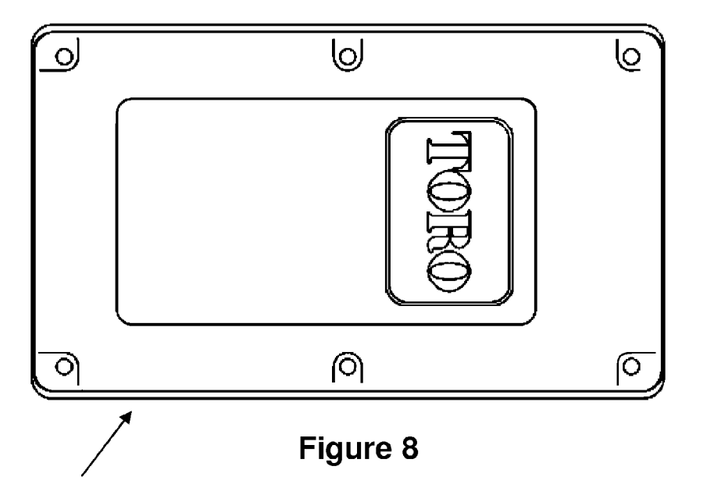
FIG. 8 illustrates a top view of a back case member of the wireless moisture sensor of FIG. 1.
Figure 9:
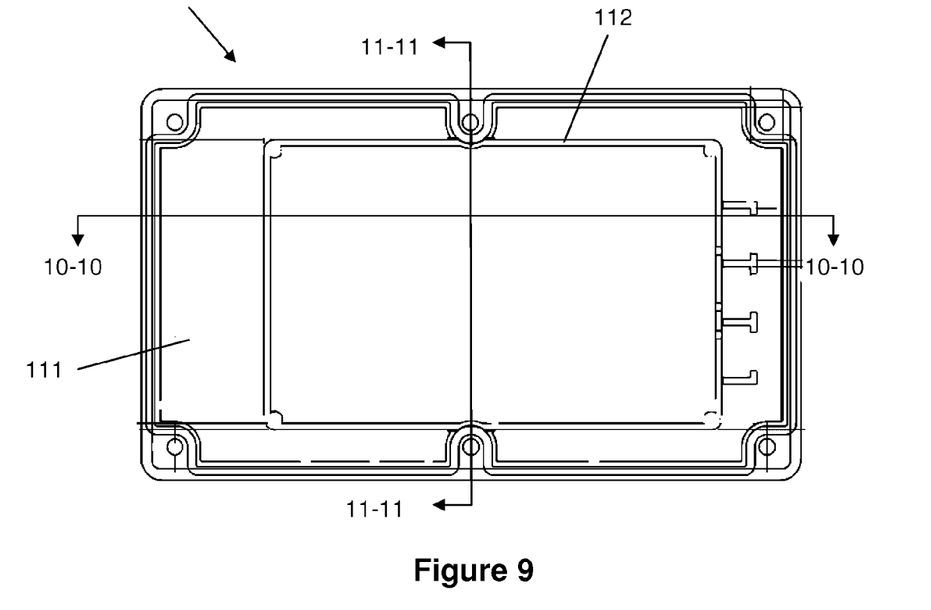
FIG. 9 illustrates a bottom view of a back case member of the wireless moisture sensor of FIG. 1.
Figure 10:
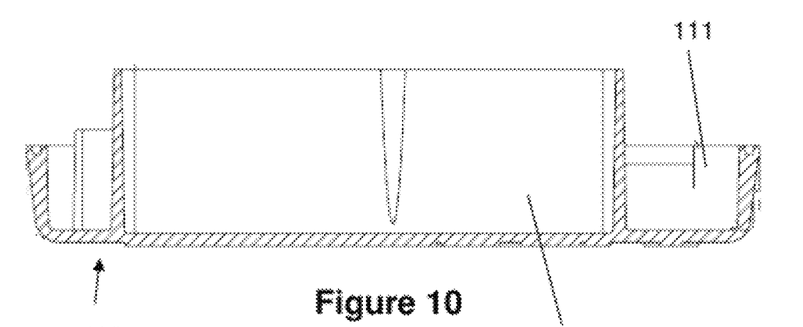
FIG. 10 illustrates a cross sectional view taken along line 10-10 in FIG. 9.
Figure 11:
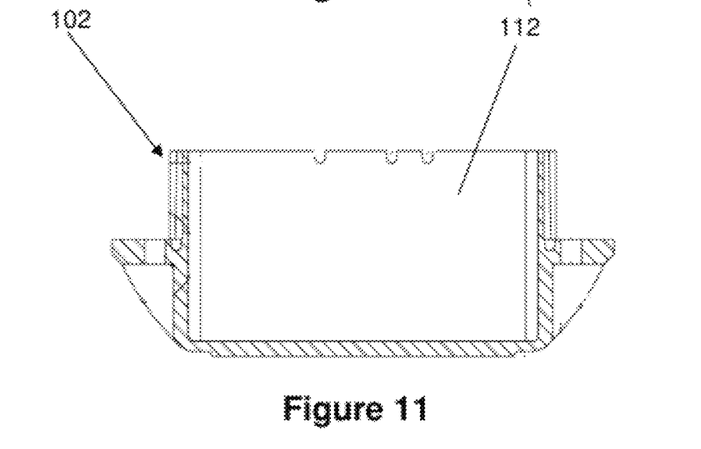
FIG. 11 illustrates a cross sectional view taken along line 11-11 in FIG. 9.
Figure 12:
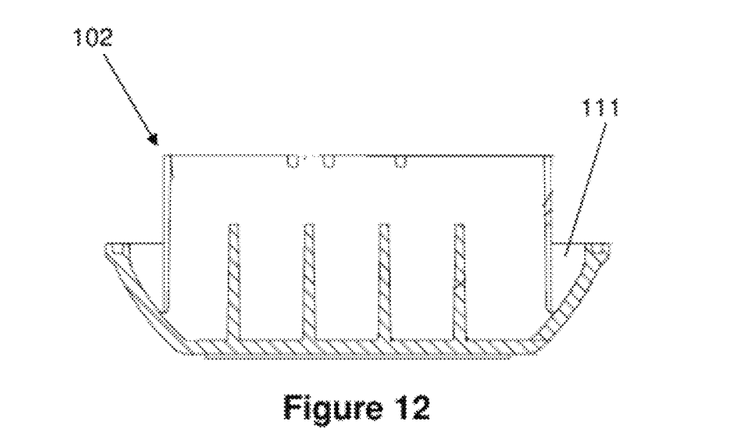
FIG. 12 illustrates a cross sectional end view of the back case member of the wireless moisture sensor of FIG. 1.

FIGS. 5-7 illustrate various views of the front case member 106. Preferably the front case member 106 forms a partial inner cavity or space for storing the internal components of the sensor 100. Similarly, as best seen in FIG. 8-12, the back case member 102 forms an outer partial cavity 111 and an inner partial cavity 112. Preferably, the front case member 106 and the back case member 102 include a tongue-in-groove connection around the adjoining regions of the members 102 and 106. A silicone seal is also preferably positioned within the tongue-in-groove connection or adjacent to it.

As previously mentioned, the sensor 100 includes features that better resist damage common to turf maintenance machines, especially those used at golf courses. One particularly damaging device used to maintain turf is an aeration tool, which typically employs elongated spikes or tines that are forced several inches into the ground.

Figure 13:
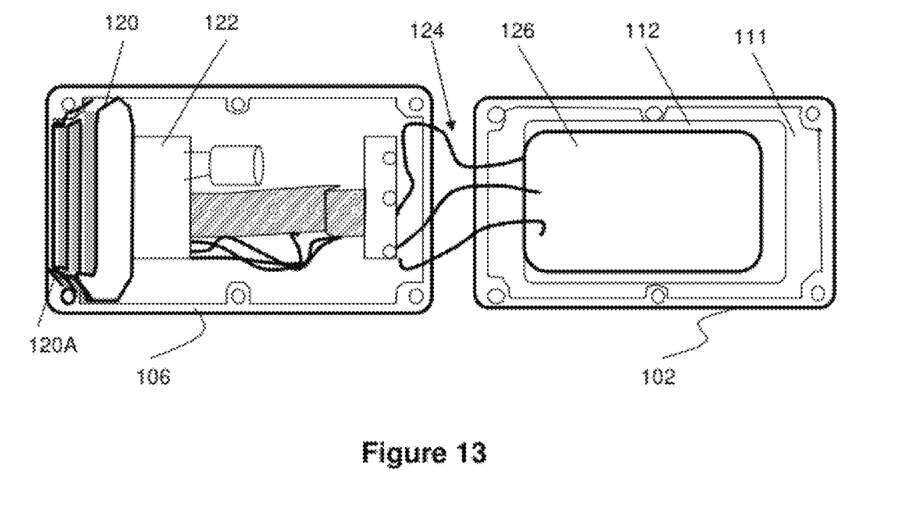
FIG. 13 illustrates a top view of an opened wireless moisture sensor of FIG. 1; and, FIG. 14 illustrates a tine-catching block within a top portion of the wireless moisture sensor of FIG. 1.
Figure 14:
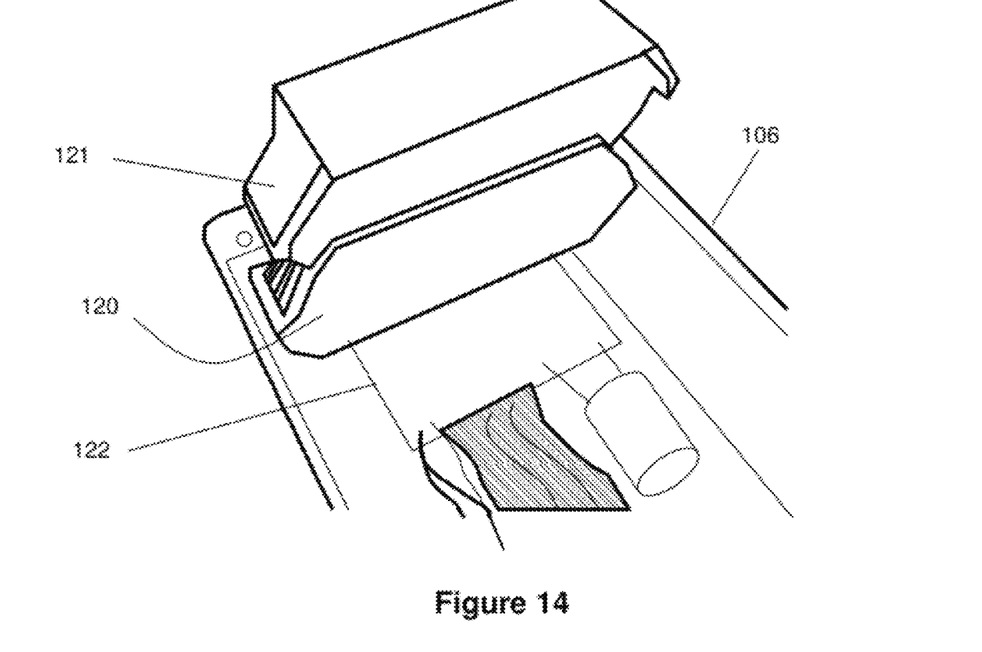

As best seen in FIGS. 13 and 14, the sensor 100 includes a tine-catching block formed of a first catcher member 120 and a second catcher member 121. Preferably, the first catcher member 120 is fixed to the front case member 106 and the second catcher member 121 is fixed to the back case member 102. The catcher members 120 and 121 preferably each include of a plurality of mating features, such as elongated, longitudinal grooves (e.g., groves 120A in FIG. 13) on each of the members 120 and 121 that allow the members 120, 121 to interlock with each other, as seen in FIG. 14.

The tine-catching block is preferably formed of a shatter-resistant material such as high-density polyethylene (HDPE). Some common plastics like ABS or Polycarbonate can be prone to shattering when impacted with a sharp metal object. In contrast, HDPE is highly resistant to shattering and can thereby absorb the energy of an incoming object. Additionally, HDPE has a dielectric constant that blocks little radio frequency energy (as opposed to metals or similar materials). In this respect, the tine-catching block can absorb the energy of an incoming tine from an aeration tool, preventing the tine from damaging internal components without restricting radio frequency transmissions by the wireless transceiver in the sensor 100.

As best seen in FIG. 13, some of the internal components of the sensor 100 are arranged in separate vertical areas of the sensor 100. Specifically, the sensor circuitry 122 (e.g., printed circuit board, microcontroller, sensor circuits) is mounted within a cavity of the front case member 102 while a battery 126 is fixed within compartment 112 in the back case member 106. When assembled, a gap is formed between the sensor circuitry 122 and the battery 126, decreasing the likelihood that an incoming tine would strike internal components of the sensor 100.

Figure 15:
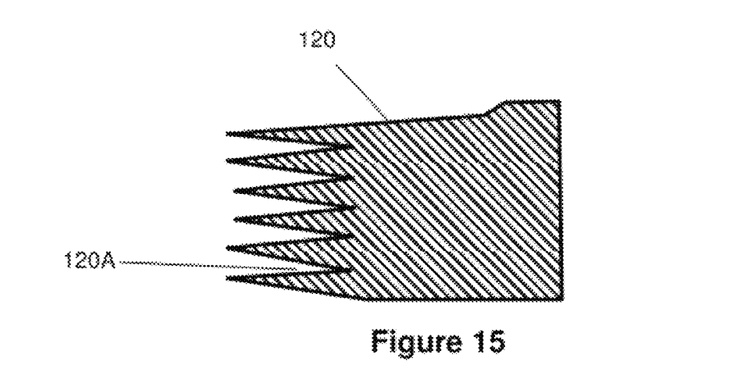
FIG. 15 illustrates a cross sectional view of a member of the tine-catching block of FIG. 14.

Optionally, the tine-catching block is preferably constructed so as to direct any incoming tines towards the center gap, further reducing any changes of damaging internal components. In one example seen in the cross section view of the catcher member 120 in FIG. 15, the tine-catching block can be constructed of thicker areas around its perimeter and a narrower region near its center to help cause deflection of a tine towards the center. In another example, the top surface of the tine-catching block can be angled towards the center and optionally have a hard top layer over the tine-catching block's perimeter (but not near the center).

To further minimize damage from tines, the sensor circuitry 122 and batteries 126 are each encapsulated with an epoxy material that helps protect from physical and water damage. Preferably, the epoxy material of the sensor circuitry 122 is separate from the epoxy surrounding the batteries 126, creating a gap near the center of the sensor 100 (e.g., the width of the gap is between 0.5" and 2"). The epoxy material helps direct an incoming tine to the gap created between the two epoxy sections while further protecting the components from water damage that may occur after the sensor 100 has been compromised.

Preferably, an epoxy material is used that does not reduce or hinder sensor readings or radio transmissions.

The sensor circuitry 122 and batteries 126 are preferably connected via wires 124 which are located near the bottom of the sensor 100. Hence, an aeration tine would need to pass through the top (i.e., near the tine catching block 120) and almost completely through the sensor 100 to damage any of the wires 124.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A soil moisture sensor comprising:
    a sensor casing having a first side with a generally flat shape and a second side opposing said first side and having a generally curved shape;
    a first plurality of elongated sensor electrode pins located on and extending out from said second side of said sensor casing;
    a second plurality of elongated sensor electrode pins located at said second side of said sensor casing and spaced apart from said first plurality of elongated sensor electrodes;
    wherein said second side has a curve that substantially matches an interior of a 4.25 inch hole.

2. The soil moisture sensor of claim 1, further comprising a tine-catching block member disposed within said sensor casing and near a top of said soil moisture sensor.

3. The soil moisture sensor of claim 2, wherein said tine-catching block member is generally thinner near a center of said block member relative to an outer periphery of said block member.

4. The soil moisture sensor of claim 1, further comprising electrical sensor components disposed within said sensor casing; said sensor components being encapsulated with an epoxy material.

5. A soil moisture sensor comprising:
    a sensor enclosure having a first side and an opposing second side;
    a plurality of sensor pins extending from said sensor enclosure in a generally perpendicular orientation relative to said first side and said second side;
    sensor circuitry disposed within said sensor enclosure; and,
    a power supply disposed within said sensor enclosure;
    wherein said sensor circuitry is located adjacent to said first side of said sensor enclosure and said power supply is disposed against said second side of said sensor enclosure so as to create a gap between said sensor circuitry and said power supply within said sensor enclosure.

6. The soil moisture sensor of claim 5, wherein said sensor circuitry and said power supply are enclosed in epoxy.

7. The soil moisture sensor of claim 5, further comprising a tine-catching block member located within said sensor enclosure and at a top end of said sensor enclosure.

8. The soil moisture sensor of claim 7, further comprising a plurality of wires connecting said sensor circuitry and said power supply, said plurality of wires located at a bottom end of said sensor enclosure.

9. A method of installing a moisture sensor comprising:
creating a cylindrical hole in soil having a diameter of about 4.25 inches;
placing a soil moisture sensor in said hole;
orienting a first group of sensor pins at a first distance from a top of said soil;
orienting a second group of sensor pins at a second distance from a top of said soil, said second distance being longer than said first distance; and,
pressing a curved surface of said soil moisture sensor into a curved wall of said cylindrical hole; said curved surface having a curved shape corresponding to and being reciprocal to a portion of said cylindrical hole having said diameter of about 4.25 inches.

10. The method of claim 9, wherein said first distance is about 4.4 inches from said top of said soil.

11. The method of claim 10, wherein said second distance is about 7-9 inches from said top of said soil.

12. The method of claim 10, wherein said pressing a curved surface of said soil moisture sensor into a curved wall of said cylindrical hole further comprises inserting said first group of sensor pins and said second group of sensor pins into undisturbed areas of said soil.

13. The method of claim 10, further comprising orienting said soil moisture sensor such that a tine-catching member within said soil moisture sensor is oriented at a top end of said soil moisture sensor.

* * * * *